United States Patent [19]
Smith et al.

[11] Patent Number: 6,037,360
[45] Date of Patent: *Mar. 14, 2000

[54] ADMINISTRATION OF 5-HT₃ RECEPTOR ANTAGONISTS TO TREAT PREMATURE EJACULATION

[75] Inventors: William L. Smith, Oakland; Paul C. Doherty, Jr., Cupertino, both of Calif.; Virgil A. Place, Kawaihae, Hi.

[73] Assignee: Vivus, Incorporated, Mountain View, Calif.

[ * ] Notice: This patent is subject to a terminal disclaimer.

[21] Appl. No.: 08/959,061

[22] Filed: Oct. 28, 1997

[51] Int. Cl.⁷ ..................... A61K 31/415; A61K 31/405
[52] U.S. Cl. ........................................... 514/397; 514/415
[58] Field of Search ...................................... 514/415, 397

[56] References Cited

U.S. PATENT DOCUMENTS

| | | |
|---|---|---|
| 3,717,634 | 2/1973 | Wu et al. . |
| 4,507,323 | 3/1985 | Stern . |
| 4,521,421 | 6/1985 | Foreman . |
| 4,766,119 | 8/1988 | Davis . |
| 4,828,544 | 5/1989 | Lane et al. ................................. 604/9 |
| 4,940,731 | 7/1990 | Bick . |
| 5,063,915 | 11/1991 | Wyckoff . |
| 5,151,448 | 9/1992 | Crenshaw et al. . |
| 5,242,391 | 9/1993 | Place et al. . |
| 5,248,699 | 9/1993 | Sysko et al. . |
| 5,276,042 | 1/1994 | Crenshaw et al. . |
| 5,327,910 | 7/1994 | Flynn . |
| 5,468,212 | 11/1995 | Shooter . |
| 5,474,535 | 12/1995 | Place et al. . |
| 5,476,121 | 12/1995 | Place et al. . |
| 5,482,039 | 1/1996 | Place et al. . |
| 5,535,758 | 7/1996 | Hagihara . |
| 5,552,429 | 9/1996 | Wong et al. ............................ 514/415 |
| 5,587,167 | 12/1996 | Choi et al. . |
| 5,597,826 | 1/1997 | Howard et al. . |
| 5,672,612 | 9/1997 | Ronsen et al. . |
| 5,707,999 | 1/1998 | Cavallini . |
| 5,922,341 | 7/1999 | Smith et al. ............................ 424/430 |

FOREIGN PATENT DOCUMENTS

| | | |
|---|---|---|
| 781 561 A1 | 7/1997 | European Pat. Off. . |
| WO 91/16021 | 10/1991 | WIPO . |
| WO 95/13072 | 5/1995 | WIPO . |
| WO 95/33048 | 10/1995 | WIPO . |
| WO 96/28142 | 9/1996 | WIPO . |

OTHER PUBLICATIONS

Balon (1996) "Antidepressants in the Treatment of Premature Ejaculation," *Journal of Sex & Marital Therapy* 22(2):85–96.

Cavallini (1995,) "Alpha–1 Blockade Pharmacotherapy in Primitive Psychogenic Premature Ejaculation Resistant to Psychotherapy," *Eur. Urology* 28:126–130.

Di Silverio et al. (1996), "Effects Comparés de l'Incision Cervico–Prostatique (ICP) et de l'Association ICP et Agonistes de la LHRH dans le Traitement de l'Hypertrophie Bénigne de la Prostate," *Journal D'Urologie* 102(3):111–116.

Falaschi et al. (1981), "Brain Dopamine and Premature Ejaculation: Results of Treatment with Dopamine Antagonists," *Apomorphine and Other Dopaminomimetics* 1:117–121.

Feinberg (1991), "Clomipramine for Obsessive–Compulsive Disorder," *AFP Clinical Pharmacology* 43(5):1735–1738.

Ferrari et al (1994), "The Selective D₂ Dopamine Receptor Antagonist Eticlopride Counteracts the Ejaculatio Praecox Induced by the Selective D₂ Dopamine Agonist SND 919 in the Rat," *Life Sciences* 55(14):1155–1162.

Hull et al. (1994), "The Roles of Nitric Oxide in Sexual Function of Male Rats," *Neuropharmacology* 33(11):1499–1504.

Metz et al. (1997), "Premature Ejaculation: A Psychophysiological Review," *Journal of Sex & Marital Therapy* 23(1):3–23.

Napoli–Farris et al. (1984), "Stimulation of Dopamine Autoreceptors Elicits Premature Ejaculation in Rats," *Pharmacology Biochemistry & Behavior* 20:69–72.

Waldinger et al. (1997), "Ejaculation–Retarding Properties of Paroxetine in Patients with Primary Premature Ejaculation: A Double–Blind, Randomized, Dose–Response Study," *British Journal of Urology* 79:592–595.

WPIDS Abstract, AN 96–188218 [19], Nomura, K. et al., WO 9609069 A1, Mar. 28, 1996.

CA Abstract, AN 119:21000, Pomerantz, S. M. et al., 1993.

Pomerantz et al., Psychopharmacology, vol. 111, pp. 47–54, 1993.

*Primary Examiner*—Minna Moezie
*Attorney, Agent, or Firm*—Dianne E. Reed; J. Elin Hartrum

[57] ABSTRACT

A method is provided for delaying the onset of ejaculation in an individual. The method involves administration of a 5-HT₃ receptor antagonist within the context of an effective dosing regimen. The preferred mode of administration is transurethral; however, the selected inhibitor may also be delivered via intracavernosal injection or using alternative routes.

23 Claims, 1 Drawing Sheet

ADMINISTRATION OF 5-HT₃ RECEPTOR ANTAGONISTS TO TREAT PREMATURE EJACULATION

TECHNICAL FIELD

This invention relates generally to methods and pharmaceutical compositions for treating sexual dysfunction; more particularly, the invention relates to treatment of premature ejaculation by administration of compounds that are 5-HT (serotonin) receptor agonists and antagonists.

BACKGROUND

Premature ejaculation is a debilitating sexual dysfunction. This dysfunction can lead to an inability to enter or sustain relationships and can cause psychological damage to sufferers. Premature ejaculation can also impair reproductive success.

Previous methods of treating premature ejaculation include psychological therapies, topical anesthetics and the use of devices (U.S. Pat. Nos. 5,535,758, 5,063,915, 5,327,910, and 5,468,212). All of these methods have significant drawbacks. Psychological therapies benefit only a subset of patients and require specialized therapists who may not be available to all patients, particularly in remote areas. Furthermore, psychological therapies cannot alleviate premature ejaculation resulting from non-psychological causes. Anesthetic agents decrease sensitivity of tissues, thereby diminishing sexual pleasure. Also, topical anesthetics can be transferred to sexual partners and thereby decrease their sensitivity and pleasure as well. With regard to devices, these can be awkward, inconvenient and embarrassing to use. Devices are highly conspicuous, and reveal the very condition which the suffering partner may prefer to conceal. Additionally, devices can cause irritation to one or both partners.

Methods for treating premature ejaculation by systemic administration of several different antidepressant compounds have been described (U.S. Pat. Nos. 4,507,323, 4,940,731, 5,151,448, and 5,276,042; PCT Publication No. WO95/13072). However, these drugs may not be effective for all patients, and the side effects of these drugs can halt treatment or impair patient compliance. Disease states or adverse interactions with other drugs may contraindicate the use of these compounds or require lower dosages that may not be effective to delay the onset of ejaculation. Additionally, the stigma of mental illness associated with antidepressant therapy can discourage patients from beginning or continuing such treatments.

Administration of the antidepressant fluoxetine has been claimed to treat premature ejaculation (U.S. Pat. No. 5,151,448). However, the administration of fluoxetine has many undesired aspects. Patients with hepatic or renal impairments may not be able to use fluoxetine due to its metabolism in the liver and excretion via the kidney. Systemic events during fluoxetine treatment involving the lungs, kidneys or liver have occurred, and death has occurred from overdoses. In addition, side effects of oral fluoxetine administration include hair loss, nausea, vomiting, dyspepsia, diarrhea, anorexia, anxiety, nervousness, insomnia, drowsiness, fatigue, headache, tremor, dizziness, convulsions, sweating, pruritis, and skin rashes. Fluoxetine interacts with a range of drugs, often by impairing their metabolism by the liver.

U.S. Pat. No. 4,940,731 describes the oral or parenteral administration of sertraline for treating premature ejaculation. It has been recognized that sertraline shares many of the same problems as fluoxetine; see Martindale, *The Extra Pharmacopoeia,* 31st edition, at p. 333 (London: The Royal Pharmaceutical Society, 1996). Sertraline is metabolized in the liver, and is excreted in the urine and feces. Thus, patients with cirrhosis must take lower doses, and caution must be exercised when administering sertraline to patients with renal impairment. Individuals taking monoamine oxidase inhibitors cannot take sertraline due to the risk of toxicity, leading to memory changes, confusion, irritability, chills, pyrexia and muscle rigidity. Side effects resulting from oral sertraline administration include nausea, diarrhea, dyspepsia, insomnia, somnolence, sweating, dry mouth, tremor and mania. Rare instances of coma, convulsions, fecal incontinence and gynecomastia have occurred in patients undergoing sertraline therapy.

U.S. Pat. No. 5,276,042 describes the administration of paroxetine for the treatment of premature ejaculation. Paroxetine is predominantly excreted in the urine, and decreased doses are recommended in patients with hepatic and renal impairments. Like sertraline, paroxetine cannot be given to patients undergoing treatment with a monoamine oxidase inhibitor. Side effects from oral administration of paroxetine include hyponatremia, asthenia, sweating, nausea, decreased appetite, oropharynx disorder, somnolence, dizziness, insomnia, tremor, anxiety, impaired micturition, weakness and paresthesia.

Thus there is a need for a method of treating premature ejaculation that requires no specialized psychological therapy, can be used conveniently and without embarrassment, and does not involve the problems associated with prior therapeutic methods.

Serotonin, or 3-(β-aminoethyl)-5-hydroxyindole (5-hydroxytryptophan, or "5-HT") is a neurotransmitter in the central nervous system which is known to play an important role in the pathogenesis of affective illness. Several different 5-HT receptor types have been identified, including 5-HT$_1$, 5-HT$_2$ and 5-HT$_3$, which are further divided into a number of different subtypes, e.g., 5-HT$_{1A}$, 5-HT$_{1B}$, 5-HT$_{1D}$, 5-HT$_{1E}$ and 5-HT$_{1F}$. It has now been discovered that administration of various serotonin agonists and antagonists is quite effective in the treatment of premature ejaculation, and addresses a number of the above-noted deficiencies in the art. Accordingly, the present invention is directed to the administration of serotonin agonists and antagonists, preferably 5-HT$_3$ receptor antagonists (also referred to herein as "5-HT$_3$ antagonists") and 5-HT$_4$ receptor agonists (also referred to herein as "5-HT$_4$ agonists"), in the treatment of premature ejaculation.

SUMMARY OF THE INVENTION

Accordingly, it is a primary object of the invention to address the above-described need in the art by providing a novel method for treating premature ejaculation by administering an effective amount of a serotonin antagonist or agonist to an individual in need of such therapy.

It is another object of the invention to provide such a method wherein the pharmacologically active agent is administered orally.

It is a further object of the invention to provide such a method wherein the pharmacologically active agent is administered parenterally.

It is another object of the invention to provide such a method wherein the pharmacologically active agent is administered buccally.

It is also an object of the invention to provide such a method wherein the pharmacologically active agent is administered nasally.

It is another object of the invention to provide such a method wherein the pharmacologically active agent is administered transurethrally.

It is an additional object of the invention to provide such a method wherein the pharmacologically active agent is administered via intracavernosal injection.

It is yet a further object of the invention to provide pharmaceutical formulations for carrying out the aforementioned method.

It is another object of the invention to provide a kit capable of use by an individual in carrying out the aforementioned method.

Additional objects, advantages and novel features of the invention will be set forth in part in the description which follows, and in part will become apparent to those skilled in the art upon examination of the following, or may be learned by practice of the invention.

In a first aspect of the invention, a method is provided for treating premature ejaculation, the method comprising administering to an individual in need of such treatment a pharmaceutical formulation containing a serotonin antagonist or agonist. Administration of the pharmaceutical formulation is carried out within the context of a predetermined dosing regimen such that the agent is effective in the treatment of premature ejaculation. Drug delivery may be accomplished through any route effective to provide relief from premature ejaculation, including oral, parenteral, buccal, rectal, topical, transdermal, transurethral, and intracavernosal injection.

In another aspect of the invention, a pharmaceutical formulation is provided for carrying out the method of the invention. The pharmaceutical formulation comprises an effective amount of a selected serotonin antagonist or agonist or a combination thereof, a pharmacologically acceptable carrier or vehicle, and, optionally (i.e., in topical, transdermal or transurethral formulations), an enhancer. Other types of components may be incorporated into the formulation as well, e.g., excipients, surfactants, preservatives (e.g., antioxidants), stabilizers, enzyme inhibitors, chelating agents, and the like, as will be appreciated by those skilled in the art of pharmaceutical formulation preparation and drug delivery.

In another aspect of the invention, a kit is provided to assist an individual in administering a drug to treat premature ejaculation. Generally, the kit will include the following components: a pharmaceutical formulation comprising an active agent as provided herein; a device for effecting delivery of the pharmaceutical formulation; a container housing the pharmaceutical formulation during storage and prior to use; and instructions for carrying out drug administration in a manner effective to delay the onset of ejaculation.

DETAILED DESCRIPTION OF THE INVENTION

Figure 1:
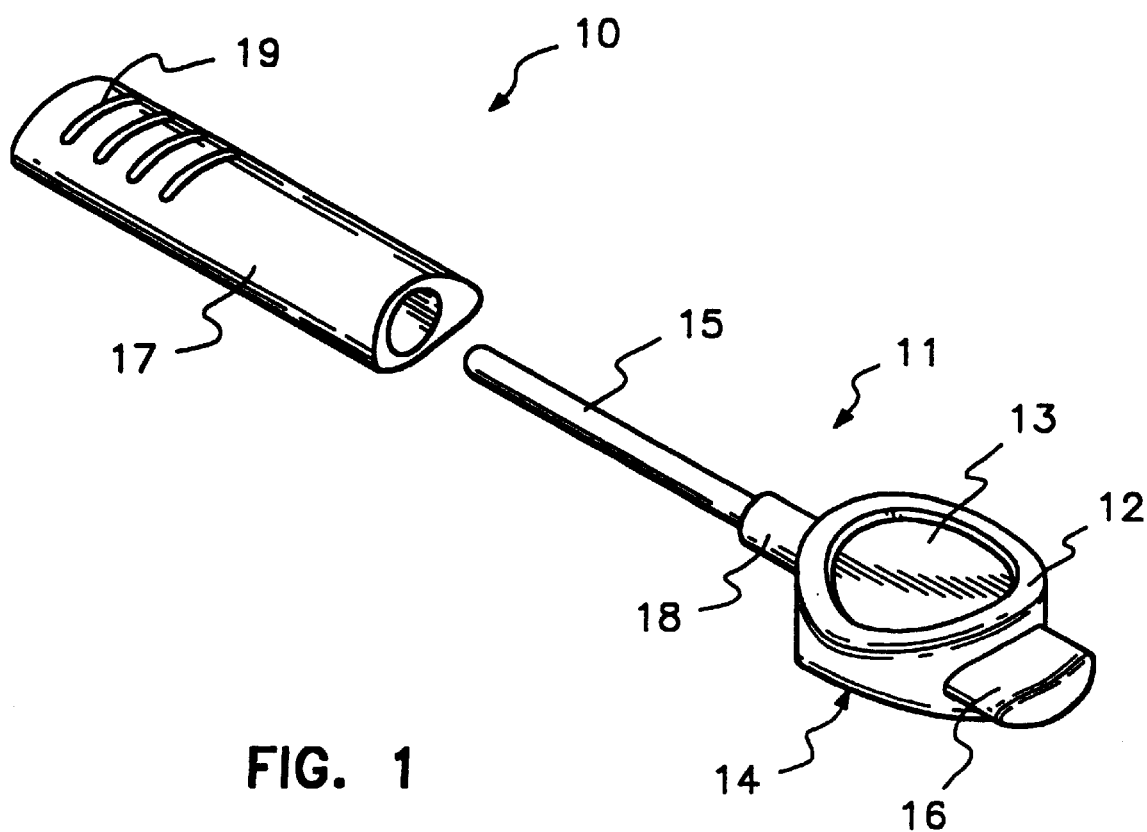
FIG. 1 illustrates an embodiment of a transurethral therapeutic device which may be used in conjunction with the present method.

Overview and Definitions:

Before describing the present invention in detail, it is to be understood that this invention is not limited to particular drugs or drug delivery systems, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to "a pharmacologically active agent" includes a combination of two or more pharmacologically active agents, reference to "a transurethral permeation enhancer" includes combinations of two or more enhancers, and the like.

In describing and claiming the present invention, the following terminology will be used in accordance with the definitions set out below.

The terms "active agent," "drug" and "pharmacologically active agent" are used interchangeably herein to refer to a chemical material or compound which, when administered to an organism (human or animal) induces a desired pharmacologic effect. Included are derivatives and analogs of those compounds or classes of compounds specifically mentioned which also induce the desired pharmacologic effect.

The terms "transurethral," "intraurethral" and "urethral" to specify the preferred mode of administration herein are used interchangeably to refer to delivery of the drug into the urethra such that the drug contacts and passes through the wall of the urethra. As noted elsewhere herein, the transurethral administration preferably involves delivery of the drug at least about 3 cm and more preferably at least about 7 cm into the urethra.

The term "intracavernosal" as used herein refers to an alternative mode of drug administration and involves injection into one or both corpora of the corpora cavernosal tissues of the penis.

By the term "transdermal" delivery, applicants intend to include both transdermal (or "percutaneous") and transmucosal administration, i.e., delivery by passage of a drug through the skin or mucosal tissue and into the bloodstream. The term "body surface" will sometimes be used herein to refer to either the skin or the mucosal tissue.

The term "topical administration" is used in its conventional sense to mean delivery of a topical drug or pharmacologically active agent to the skin or mucosa.

"Penetration enhancement" or "permeation enhancement" as used herein relates to an increase in the permeability of the urethral wall to the selected pharmacologically active agent, i.e., so that the rate at which the drug permeates through the urethral wall is increased.

"Carriers" or "vehicles" as used herein refer to carrier materials suitable for drug administration. Carriers and vehicles useful herein include any such materials known in the art, e.g., any liquid, gel, solvent, liquid diluent, solubilizer, or the like, which is nontoxic and which does not interact with other components of the composition in a deleterious manner.

The term "premature ejaculation" as used herein intends a sexual dysfunction wherein a male is unable to control the ejaculatory process to a degree sufficient to satisfy a partner. Generally, "premature ejaculation" refers to persistent or recurring ejaculation with minimal stimulation before or during sexual intercourse. The term includes both "congenital" or "lifelong" premature ejaculation and "primary" or "acquired" premature ejaculation as set forth, for example, in U.S. Pat. No. 5,151,448, and in *Male Infertility and Sexual Dysfunction* at p. 356 (New York: Springer-Verlag, 1997). See also *Diagnostic and Statistical Manual of Mental Disorders* (Washington, D.C.: American Psychiatric Association, 1994).

By an "effective" amount of a drug or pharmacologically active agent is meant a nontoxic but sufficient amount of the drug or agent to provide the desired effect.

Active Agents for Treating Premature Ejaculation:

In order to carry out the method of the invention, a selected pharmacologically active agent is administered to an individual with a history of premature ejaculation. The active agent may be administered orally, parenterally, buccally, rectally, or locally by intracavernosal injection or by delivery to the urethra. Suitable pharmacologically active agents include, but are not limited to:

serotonin agonists including 2-methyl serotonin, buspirone, ipsaperone, tiaspirone, gepirone, D-lysergic acid diethylamide ("LSD"), ergot alkaloids, 8-hydroxy-(2-N,N-dipropylamino)-tetraline, 1-(4-bromo-2,5-dimethoxyphenyl)-2-aminopropane, cisapride, sumatriptan, m-chlorophenylpiperazine, trazodone, zacopride and mezacopride; and serotonin antagonists including ondansetron, granisetron, metoclopramide, tropisetron, dolasetron, palonosetron, trimethobenzamide, methysergide, risperidone, ketanserin, ritanserin, clozapine, amitriptyline, MDL 100,507 (Marion Merrell Dow), azatadine, cyproheptadine, fenclonine, chlorpromazine and mianserin.

Serotonin, or 5-HT, plays a variety of roles throughout the body, regulating smooth muscle and platelet function, and acting as a neurotransmitter in the central nervous system. Serotonin acts through specific cellular receptors which comprise at least 15 individual subtypes. These receptors can be grouped into at least four families based on structural and functional characteristics. The $5\text{-}HT_1$, $5\text{-}HT_2$ and $5\text{-}HT_4$ families are G-protein coupled receptors linked to enzymatic and electrical effector systems, while the $5\text{-}HT_3$ receptor is a gated ion channel. Serotonin agonists are agents which mimic the effect of serotonin on at least one serotonin receptor subtype. For example, $5\text{-}HT_4$ agonists mimic the effect of serotonin on at least one $5\text{-}HT_4$ receptor. Conversely, serotonin antagonists are agents which block the effect of serotonin on at least one serotonin receptor subtype; $5\text{-}HT_3$ antagonists block the effect of serotonin on the $5\text{-}HT_3$ receptor.

Preferred active agents are $5\text{-}HT_3$ antagonists and $5\text{-}HT_4$ agonists. $5\text{-}HT_3$ receptors can be found, for example, on parasympathetic terminals in the gastrointestinal tract and in the central nervous system, both of which participate in the emetic response. $5\text{-}HT_4$ receptors are found throughout the body, including on nerve terminals in the CNS, the gastrointestinal tract, and on smooth muscle and secretory cells. $5\text{-}HT_4$ receptors activate adenylyl cyclase, and are involved in the regulation of secretion and peristalsis. Examples of $5\text{-}HT_3$ antagonists include ondansetron, ergot alkaloids, granisetron, metoclopramide, trimethobenzamide, tropisetron, dolasetron, batanopride and zacopride. Examples of $5\text{-}HT_4$ agonists include cisapride and D-lysergic acid diethylamide.

The active agents may be administered in the form of pharmaceutically acceptable salts, esters, amides or prodrugs or combinations thereof. However, conversion of inactive ester, amide or prodrug forms to an active form must occur prior to or upon reaching the target tissue or cell. Salts, esters, amides and prodrugs of the active agents may be prepared using standard procedures known to those skilled in the art of synthetic organic chemistry and described, for example, by J. March, *Advanced Organic Chemistry: Reactions, Mechanisms and Structure*, 4th Ed. (New York: Wiley-Interscience, 1992). For example, acid addition salts are prepared from the free base (typically wherein the neutral form of the drug has a neutral —$NH_2$ group) using conventional means, involving reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, ptoluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Conversely, preparation of basic salts of acid moieties which may be present on a drug are prepared in a similar manner using a pharmaceutically acceptable base such as sodium hydroxide, potassium hydroxide, ammonium hydroxide, calcium hydroxide, trimethylamine, or the like. Preparation of esters involves functionalization of hydroxyl and/or carboxyl groups which may be present within the molecular structure of the drug. The esters are typically acyl-substituted derivatives of free alcohol groups, i.e., moieties which are derived from carboxylic acids of the formula RCOOH where R is alkyl, and preferably is lower alkyl. Esters can be reconverted to the free acids, if desired, by using conventional hydrogenolysis or hydrolysis procedures. Preparation of amides and prodrugs can be carried out in an analogous manner.

Other derivatives and analogs of the active agents may be prepared using standard techniques known to those skilled in the art of synthetic organic chemistry, or may be deduced by reference to the pertinent literature. In addition, chiral active agents may be in enantiomerically pure form, or they may be administered as an enantiomeric mixture.

Pharmaceutical Formulations and Modes of Administration:

Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, may include other pharmaceutical agents, adjuvants, diluents, buffers, etc. The compounds may thus be administered orally, parenterally, transdermally, rectally, nasally, buccally, topically or via an implanted reservoir in dosage formulations containing conventional non-toxic pharmaceutically acceptable carriers, adjuvants and vehicles. The term "parenteral" as used herein is intended to include subcutaneous, intravenous, and intramuscular injection. The amount of active compound administered will, of course, be dependent on the subject being treated, the subject's weight, the manner of administration and the judgment of the prescribing physician.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan mono-laurate, triethanolamine sodium acetate, triethanolamine oleate, etc. Actual methods of preparing such dosage forms are known, or will be apparent, to those skilled in this art; for example, see *Remington's Pharmaceutical Sciences*, referenced above.

For oral administration, the composition will generally take the form of a tablet or capsule, or may be an aqueous or nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

Parenteral administration, if used, is generally characterized by injection. Injectable formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils, fatty esters or polyols are conventionally employed as solvents or suspending media. A more recently revised approach for parenteral administration involves use of a slow release or sustained release system, such that a constant level of dosage is maintained. See, e.g., U.S. Pat. No. 3,710,795.

Intracavernosal injection can be carried out by use of a syringe any other suitable device. An example of a hypodermic syringe useful herein, that can be used for simultaneous injection into both corpora, is described in U.S. Pat. No. 4,127,118 to Latorre. The injection is made on the dorsum of the penis by placement of the needle to the side of each dorsal vein and inserting it deep into the corpora.

The active agent can be administered in a pharmaceutical formulation suitable for transurethral drug delivery. The formulation contains one or more selected carriers or excipients, such as water, silicone, waxes, petroleum jelly, polyethylene glycol ("PEG"), propylene glycol ("PG"), liposomes, sugars such as mannitol and lactose, and/or a variety of other materials, with polyethylene glycol and derivatives thereof particularly preferred.

Depending on the drug administered, it may be desirable to incorporate a transurethral permeation enhancer in the urethral dosage form. Examples of suitable transurethral permeation enhancers include dimethylsulfoxide ("DMSO"), dimethyl formamide ("DMF"), N,N-dimethylacetamide ("DMA"), decylmethylsulfoxide ("$C_{10}$MSO"), polyethylene glycol monolaurate ("PEGML"), glycerol monolaurate, lecithin, the 1-substituted azacycloheptan-2-ones, particularly 1-n-dodecylcyclazacycloheptan-2-one (available under the trademark Azone® from Nelson Research & Development Co., Irvine, Calif.), SEPA® (available from Macrochem Co., Lexington, Mass.), alcohols (e.g., ethanol), detergents (such as Tergitol®, Nonoxynol-9® and TWEEN-80®) and the like.

Transurethral formulations may additionally include one or more enzyme inhibitors effective to inhibit drug-degrading enzymes which may be present in the urethra. Such enzyme inhibiting compounds may be determined by those skilled in the art by reference to the pertinent literature and/or using routine experimental methods. Additional optional components include excipients, preservatives (e.g., antioxidants), chelating agents, solubilizing agents (e.g., surfactants), and the like, as will be appreciated by those skilled in the art of drug formulation preparation and delivery.

Transurethral drug administration, as explained in PCT Publication WO91/16021, entitled "Treatment of Erectile Dysfunction," can be carried out in a number of different ways using a variety of urethral dosage forms. For example, the drug can be introduced into the urethra from a flexible tube, squeeze bottle, pump or aerosol spray. The drug may also be contained in coatings, pellets or suppositories which are absorbed, melted or bioeroded in the urethra. In certain embodiments, the drug is included in a coating on the exterior surface of a penile insert. A preferred drug delivery device for administering a drug transurethrally is shown in FIG. 1. It is preferred, although not essential, that the drug be delivered at least about 3 cm into the urethra, and preferably at least about 7 cm into the urethra. Generally, delivery at about 3 cm to about 8 cm into the urethra will provide effective results in conjunction with the present method.

Urethral suppository formulations containing PEG or a PEG derivative are particularly preferred urethral dosage forms herein, and may be conveniently formulated using conventional techniques, e.g., compression molding, heat molding or the like, as will be appreciated by those skilled in the art and as described in the pertinent literature and pharmaceutical texts. See, for example, *Remington: The Science and Practice of Pharmacy,* 19th Ed. (Easton, PA: Mack Publishing Co., 1995), which discloses typical methods of preparing pharmaceutical compositions in the form of urethral suppositories. The PEG or PEG derivative preferably has a molecular weight $M_w$ in the range of about 200 to 2500, more preferably in the range of about 1000 to 2000. Suitable polyethylene glycol derivatives include polyethylene glycol fatty acid esters, for example, polyethylene glycol monostearate, polyethylene glycol sorbitan esters, e.g., polysorbates, and the like. It is also preferred that urethral suppositories contain one or more solubilizing agents effective to increase the solubility of the active agent in the PEG or other transurethral vehicle.

The solubilizing agent may be a nonionic, anionic, cationic or amphoteric surfactant. Nonionic surfactants include: long-chain fatty acids, i.e., acids having the structural formula $CH_3(CH_2)_m COOH$ where m is an integer in the range of 8 to 16; fatty alcohols, that is, alcohols having the structural formula $CH_3(CH_2)_m C(H)OH$, such as lauryl, cetyl and stearyl alcohols; glyceryl esters such as the naturally occurring mono-, di- and triglycerides; and esters of fatty alcohols or other alcohols such as propylene glycol, polyethylene glycol, sorbitan, sucrose, and cholesterol. Examples of water-soluble nonionic surfactant derivatives include sorbitan fatty acid esters (such as those sold under the tradename Span®), polyoxyethylene sorbitan fatty acid esters (such as those sold under the tradename TWEEN®), polyoxyethylene fatty acid esters (such as those sold under the tradename Myrj®), polyoxyethylene steroidal esters, polyoxypropylene sorbitan fatty acid esters, polyoxypropylene fatty acid esters, polyoxypropylene steroidal esters, polyoxyethylene ethers (such as those sold under the tradename Brij®), polyglycol ethers (such as those sold under the tradename Tergitol®), and the like. Preferred nonionic surfactants for use as the solubilizing agent herein are polyglycol ether, polyoxyethylene sorbitan trioleate, sorbitan monopalmitate, polysorbate 80, polyoxyethylene 4-lauryl ether, propylene glycol, and mixtures thereof. Anionic surfactants which may be used as the solubilizing agent herein include long-chain alkyl sulfonates, carboxylates, and sulfates, as well as alkyl aryl sulfonates, and the like. Preferred anionic surfactants are sodium dodecyl sulfate, dialkyl sodium sulfosuccinate (e.g., sodium bis(2-ethylhexyl)-sulfosuccinate), sodium 7-ethyl-2-methyl-4-dodecyl sulfate and sodium dodecylbenzene sulfonate. Cationic surfactants which may be used to solubilize the active agent are generally long-chain amine salts or quaternary ammonium salts, e.g., decyltrimethylammonium bromide, dodecyltrimethylammonium bromide, tetradecyltrimethylammonium bromide, tetradecyltrimethylammonium chloride, and the like. Amphoteric surfactants are generally, although not necessarily, compounds which include a carboxylate or phosphate group as the anion and an amino or quaternary ammonium moiety as the cation. These include, for example, various polypeptides, proteins, alkyl betaines, and natural phospholipids such as lecithins and cephalins. Other suitable solubilizing agents include glycerin, propylene glycol, fatty acids and fatty alcohols. The solubilizing agent will be present in the range of approximately 0.01 wt. % to 40 wt. %, more preferably in the range of approximately 5.0 wt. % to 40 wt. %, and most preferably in the range of approximately 10.0 wt. % to 40 wt. %.

It may be desirable to deliver the active agent in a urethral dosage form which provides for controlled or sustained release of the agent. In such a case, the dosage form typically comprises a biocompatible, biodegradable material, typically a biodegradable polymer. Examples of such polymers include polyester, polyalkylcyanoacrylate, polyorthoester, polyanhydride, albumin, gelatin and starch. As explained, for example, in PCT Publication No. WO96/40054, these and other polymers can be used to provide biodegradable microparticles which enable controlled and sustained drug release, in turn minimizing the required dosing frequency.

The urethral suppository will preferably, although not necessarily, be on the order of 2 to 20 mm, preferably 5 to 10 mm in length and less than about 5 mm, preferably less than about 2 mm in width. The weight of the suppository form will typically be in the range of approximately 1 mg to 50 mg. However, it will be appreciated by those skilled in the art that the size of the suppository can and will vary, depending on the potency of the drug, the nature of the formulation, and other factors.

In FIG. 1, a suitable transurethral drug delivery device is shown generally at 10. The device comprises a transurethral inserter 11 having an easily graspable segment 12 that has opposing symmetrically concave surfaces 13 and 14 adapted to be held by two fingers. Drug is contained within a urethral suppository (not shown) within shaft 15, which is sized to fit within the urethra. A longitudinal plunger, the tip of which is seen at 16, is slidably insertable into the longitudinal bore contained within shaft 15. To extrude drug into the urethra, shaft 15 is inserted into the urethra, and plunger tip 16 is pushed into segment 12. The inserter 11 is then removed. Prior to use, and during storage, the device is capped with elongate cap 17 which fits snugly over flange 18 at the proximal end of shaft 15. The cap 17 is provided with a series of parallel ridges 19 to facilitate gripping of the cap and removal from inserter 11.

Although the transurethral drug delivery device shown in FIG. 1 represents a preferred device for use herein, again, it should be emphasized that a wide variety of device configurations and urethral dosage forms can be used.

Examples of other devices suited to deliver a drug transurethrally are those described and illustrated in PCT Publication No. WO91/16021.

The devices can either be manufactured under sterile conditions, thereby eliminating the need for post-manufacturing sterilization, or they can be manufactured under non-sterile conditions and then subsequently sterilized by any suitable technique, e.g., radiation sterilization. The devices can be manufactured by typical plastic forming and coating processes known in the art, including molding extrusion, heat forming, dip coating, and the like.

The method of drug delivery herein may involve an "active" delivery mechanism such as iontophoresis, electroporation or phonophoresis. Devices and methods for delivering drugs in this way are well known in the art. Iontophoretically assisted drug delivery is, for example, described in PCT Publication No. WO96/40054, cited above. Briefly, the active agent is driven through the urethral wall by means of an electric current passed from an external electrode to a second electrode contained within or affixed to a urethral probe.

The compounds of the invention may also be delivered through the skin using conventional transdermal drug delivery systems, i.e., transdermal "patches" wherein the agent is typically contained within a laminated structure that serves as a drug delivery device to be affixed to the skin. In such a structure, the drug composition is typically contained in a layer, or "reservoir," underlying an upper backing layer. The laminated device may contain a single reservoir, or it may contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form.

The backing layer in these laminates, which serves as the upper surface of the device, functions as the primary structural element of the laminated structure and provides the device with much of its flexibility. The material selected for the backing material should be selected so that it is substantially impermeable to the active agent and any other materials that are present. The backing layer may be either occlusive or nonocclusive, depending on whether it is desired that the skin become hydrated during drug delivery. The backing is preferably made of a sheet or film of a preferably flexible elastomeric material. Examples of polymers that are suitable for the backing layer include polyethylene, polypropylene, polyesters, and the like.

During storage and prior to use, the laminated structure includes a release liner. Immediately prior to use, this layer is removed from the device to expose the basal surface thereof, either the drug reservoir or a separate contact adhesive layer, so that the system may be affixed to the skin.

The release liner should be made from a drug/vehicle impermeable material.

Transdermal drug delivery devices may be fabricated using conventional techniques, known in the art, for example by casting a fluid admixture of adhesive, drug and vehicle onto the backing layer, followed by lamination of the release liner. Similarly, the adhesive mixture may be cast onto the release liner, followed by lamination of the backing layer. Alternatively, the drug reservoir may be prepared in the absence of drug or excipient, and then loaded by "soaking" in a drug/vehicle mixture.

The laminated transdermal drug delivery systems may in addition contain a skin permeation enhancer. That is, because the inherent permeability of the skin to some drugs may be too low to allow therapeutic levels of the drug to pass through a reasonably sized area of unbroken skin, it is necessary to coadminister a skin permeation enhancer with such drugs. Suitable enhancers are well known in the art.

Alternatively, the pharmaceutical compositions of the invention may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions of the invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, propellants such as fluorocarbons or nitrogen, and/or other conventional solubilizing or dispersing agents.

Preferred formulations for topical drug delivery are ointments and creams. Ointments are semisolid preparations which are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Formulations for buccal administration include tablets, lozenges, gels and the like. Alternatively, buccal administration can be effected using a transmucosal delivery system as known to those skilled in the art.

The pharmaceutical formulation may contain one or more pharmacologically active agents in addition to the serotonin agonist or antagonist. Vasoactive agents, particularly vasodilators, are preferred additional agents.

Suitable vasoactive agents include, but are not limited to: nitrates such as nitroglycerin, isosorbide dinitrate, erythrityl tetranitrate, amyl nitrate, sodium nitroprusside, molsidomine, linsidomine chlorhydrate ("SIN-1"), S-nitroso-N-acetyl-d,1-penicillamine ("SNAP"), S-nitroso-N-cysteine and S-nitroso-N-glutathione ("SNO-GLU"); long and short acting α-blockers such as phenoxybenzamine, dibenamine, doxazosin, terazosin, phentolamine, tolazoline, prazosin, trimazosin, alfuzosin, tamsulosin and indoramin; ergot alkaloids such as ergotamine and ergotamine analogs, e.g., acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride and terguride; antihypertensive agents such as diazoxide, hydralazine and minoxidil; vasodilators such as nimodepine, pinacidil, cyclandelate, dipyridamole and isoxsuprine; chlorpromazine; haloperidol; yohimbine; Rec15/2739; trazodone; naturally occurring prostaglandins such as $PGE_0$, $PGE_1$, $PGA_1$, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_{3\alpha}$; semisynthetic or synthetic derivatives of natural prostaglandins, including carboprost tromethamine, dinoprost tromethamine, dinoprostone, lipoprost, gemeprost, metenoprost, sulprostone and tiaprost; and vasoactive intestinal peptides. Prazosin, prostaglandin $E_0$, prostaglandin $E_1$ and prostaglandin $E_2$ are particularly preferred vasoactive agents to be co-administered with the active agent.

The amount of active agent administered, and the dosing regimen used, will, of course, be dependent on the particular drug selected, the age and general condition of the subject being treated, the severity of the subject's condition, and the judgment of the prescribing physician. Generally, the daily dosage when administered locally will be less than the dosage normally given in conjunction with systemic modes of administration, and typically, the drug will be administered one to four times daily or, with some active agents, just prior to intercourse. Alternatively, a large initial loading dose can be used to achieve effective levels of the agent and can be followed by smaller doses to maintain those levels. A typical daily dose of an active agent as administered locally is generally in the range of approximately 0.1 to 500 mg. Depending on the half-life of the drug and the availability via the chosen route of administration, the dosing regimen can be modulated in order to achieve satisfactory control of the onset of ejaculation.

Kits:

The invention also encompasses a kit for patients to carry out the present method of treating premature ejaculation. The kit contains the pharmaceutical formulation to be administered, a device for administering the formulation (e.g., a transurethral drug delivery device such as shown in FIG. 1, or a syringe), a container, preferably sealed, for housing the drug and device during storage and prior to use, and instructions for carrying out drug administration in an effective manner. The formulation may consist of the drug in unit dosage form. The kit may contain multiple formulations of different dosages of the same agent. The kit may also contain multiple formulations of different active agents. The instructions may be in written or pictograph form, or can be on recorded media including audio tape, video tape, or the like.

Use in Conjunction with Venous Flow Control ("VFC") Device:

In an alternative embodiment of the invention, the pharmacologically active agent is administered in combination with a venous flow control device such as that described in commonly assigned U.S. patent application Ser. No. 08/782, 867, filed Jan. 10, 1997, entitled "Venous Flow Control Element for Maintaining Penile Erection" now U.S. Pat. No.

5,855,548. Preferred devices are formed from a length of flexible tubing having an integral fastening means, so as to provide for readily adjustable venous flow control when applied to the penis. The device is applied to the base of the penis prior to and during sexual intercourse, such that it effectively enhances retention of blood within the penis without substantially obstructing arterial inflow or becoming too constrictive during the erectile process. Use of the VFC device also enables enhanced effectiveness of local drug therapy, in that the active agent is retained within the penis, allowing movement into the corpus cavernosa. This produces smooth muscle response and a consistent erectile response. In this embodiment, a kit will include the venous flow control device in addition to the components noted above, along with instructions for using the device.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entirety.

EXAMPLE 1

A pharmaceutical formulation for transurethral administration is prepared by mixing 0.1–25 mg of the serotonin agonist sumatriptan with polyethylene glycol, molecular weight ($M_w$) approximately 4000, and heating the mixture to a temperature just high enough to produce a sumatriptan-polymer melt. The sumatriptan-glycol mixture can then be poured into a mold suitable to provide a sumatriptan suppository approximately 5 mm in length and 1.5 mm in width, and allowed to cool. The suppository so provided is a unit dosage form suitable for transurethral administration. If desired, the sumatriptan-glycol mixture may be allowed to cool on the tip of a rod adapted to be inserted into the urethra.

EXAMPLE 2

The procedure of Example 1 is repeated, except that 1–50 mg of the serotonin agonist cisapride is substituted for sumatriptan. A suppository suitable for transurethral administration of a unit dosage of cisapride is thus provided.

EXAMPLE 3

The procedure of Example 1 is repeated, except that 0.1–25 mg of the serotonin antagonist risperidone is substituted for sumatriptan. A suppository suitable for transurethral administration of a unit dosage of risperidone is thus provided.

EXAMPLE 4

The procedure of Example 1 is repeated, except that 1–100 mg of the serotonin antagonist clozapine is substituted for sumatriptan. A suppository suitable for transurethral administration of a unit dosage of clozapine is thus provided.

EXAMPLE 5

The procedures of the foregoing Examples are repeated, except that cocoa butter is substituted for polyethylene glycol.

EXAMPLE 6

A penile insert coated with a serotonin agonist or antagonist is prepared as follows. An ethylene vinyl acetate (28% VA) rod is formed into an insert having a shaft approximately 10 cm long with a spherical, blunted tip. A dipping bath comprising a 50—50 weight blend of PEG 1450 and PEG 4000 and sufficient agent to attain the desired concentration in the coating is prepared and heated to 70° C. The insert is suspended by its head, dipped into the dipping bath and removed. A penile insert suitable for transurethral administration of agent is thus provided.

EXAMPLE 7

A pharmaceutical formulation suitable for injection can be made by dissolving 4 mg of the 5-$HT_3$ antagonist ondansetron hydrochloride dihydrate, 9.0 mg of sodium chloride, 0.5 mg of citric acid monohydrate and 0.25 mg of sodium citrate dihydrate in water to give a 2 mL solution.

EXAMPLE 8

A pharmaceutical formulation suitable for oral administration can be prepared by admixing either 4 or 8 mg of the 5-$HT_3$ antagonist ondansetron hydrochloride dihydrate with appropriate amounts of lactose, microcrystalline cellulose, pregelatinized starch, hydroxypropyl methylcellulose, magnesium stearate and titanium dioxide and forming the mixture into tablets.

EXAMPLE 9

A pharmaceutical formulation suitable for oral administration can be made suspending the 5-$HT_4$ agonist cisapride monohydrate at 1 mg/mL in an aqueous solution containing appropriate amounts of sodium chloride, hydroxypropyl methylcellulose, methylparaben, microcrystalline cellulose and carboxymethylcellulose sodium, polysorbate 20, propylparaben, and sorbitol.

EXAMPLE 10

A pharmaceutical formulation suitable for oral administration can be prepared by admixing either 10 or 20 mg of the 5-$HT_4$ agonist cisapride monohydrate with appropriate amounts of lactose monohydrate, microcrystalline cellulose, polysorbate 20, povidone, corn starch, magnesium stearate and colloidal silicon dioxide and forming the mixture into tablets.

EXAMPLE 11

Individuals are assessed and pre-screened to assemble an experimental group of subjects prone to premature ejaculation. The formulations prepared in the preceding Examples are administered to the individuals and evaluated with respect to the capability of delaying the onset of ejaculation. The dosage regimen can be altered for subjects not experiencing improvement in their ability to delay the onset of ejaculation. Alternatively, different active agents can be administered to subjects not experiencing improvement. Each of the formulations prepared and administered is expected to be effective in treating premature ejaculation.

EXAMPLE 12

The procedure of Example 11 is repeated, except that a flexible, adjustable venous flow control device is used prior to and during sexual intercourse, in combination with the drug therapy described. Substantially the same results are expected.

We claim:

1. A method for treating an individual with a history of premature ejaculation, comprising administering to the individual an effective amount of a pharmaceutical formulation comprising a 5-$HT_3$ receptor antagonist as the active agent wherein the active agent of the formulation is effective to delay the onset of ejaculation by the individual during sexual intercourse.

2. The method of claim 1, wherein the formulation is administered transurethrally.

3. The method of claim 1, wherein the formulation is administered by intracavernosal injection.

4. The method of claim 1, wherein the formulation is administered transdermally.

5. The method of claim 1, wherein the formulation is administered topically.

6. The method of claim 1, wherein the formulation is administered orally.

7. The method of claim 1, wherein the formulation is administered parenterally.

8. The method of claim 1, wherein the formulation is administered buccally.

9. The method of claim 1, wherein the formulation is administered nasally.

10. The method of claim 1, wherein a predetermined dose of the agent is administered to the individual one to four times in a twenty-four hour period.

11. The method of claim 1, wherein the pharmaceutical formulation further comprises a vasoactive agent.

12. The method of claim 2, wherein the pharmaceutical formulation comprises a urethral suppository.

13. The method of claim 12, wherein the urethral suppository contains a pharmacologically acceptable carrier comprised of polyethylene glycol.

14. The method of claim 13, wherein the urethral suppository further includes a solubilizing compound for increasing the solubility of the agent in the carrier.

15. The method of claim 1, wherein the 5-$HT_3$ receptor antagonist is selected from the group consisting of ondansetron, ergot alkaloids, granisetron, trimethobenzamide, tropisetron, dolasetron, batanopride and zacopride.

16. The method of claim 15, wherein the 5-$HT_3$ receptor antagonist is ondansetron.

17. The method of claim 15, wherein the 5-$HT_3$ receptor antagonist is an ergot alkaloid.

18. The method of claim 15, wherein the 5-$HT_3$ receptor antagonist is granisetron.

19. The method of claim 15, wherein the 5-$HT_3$ receptor antagonist is trimethobenzamide.

20. The method of claim 15, wherein the 5-$HT_3$ receptor antagonist is tropisetron.

21. The method of claim 15, wherein the 5-$HT_3$ receptor antagonist is dolasetron.

22. The method of claim 15, wherein the 5-$HT_3$ receptor antagonist is batanopride.

23. The method of claim 15, wherein the 5-$HT_3$ receptor antagonist is zacopride.

* * * * *